United States Patent
Smith et al.

(10) Patent No.: US 11,501,876 B2
(45) Date of Patent: Nov. 15, 2022

(54) SYSTEM AND PROCESS DISTRIBUTING PHYSICIAN-OWNED DURABLE MEDICAL EQUIPMENT (DME)

(71) Applicant: Rx Redefined, Inc., Oakland, CA (US)

(72) Inventors: Erik Smith, Oakland, CA (US); Brandon Boots, Oakland, CA (US)

(73) Assignee: RX Redefined, Inc., Oakland, CA (US)

( * ) Notice: Subject to any disclaimer, the term of this patent is extended or adjusted under 35 U.S.C. 154(b) by 11 days.

(21) Appl. No.: 17/086,202

(22) Filed: Oct. 30, 2020

(65) Prior Publication Data

US 2021/0295988 A1 Sep. 23, 2021

Related U.S. Application Data

(60) Provisional application No. 62/928,260, filed on Oct. 30, 2019.

(51) Int. Cl.
*G16H 40/40* (2018.01)
*G16H 50/20* (2018.01)

(52) U.S. Cl.
CPC ............. *G16H 40/40* (2018.01); *G16H 50/20* (2018.01)

(58) Field of Classification Search
CPC ........ G16H 40/40; G16H 50/20; G16H 40/20; G06Q 10/10; G06Q 50/22
See application file for complete search history.

(56) References Cited

U.S. PATENT DOCUMENTS

2002/0133376 A1* 9/2002 Fritschen ........... H04N 1/32101
705/2

FOREIGN PATENT DOCUMENTS

CA 3051676 A1 * 8/2018 ........... A61B 5/4818

OTHER PUBLICATIONS

Trac Medical Solutions Inks Agreement with Apria Healthcare to Implement CareCert Electronic Form Processing Solution. Business Wire Mar. 4, 2004: 5176. (Year: 2004).*

* cited by examiner

*Primary Examiner* — Linh Giang Le
(74) *Attorney, Agent, or Firm* — Weintraub Tobin; Eric Caligiuri

(57) ABSTRACT

Provided is a distribution platform for physician-owned Durable Medical Equipment (DMEs). In the platform, the system authenticates a physician and selects or creates a patient, and determines a set of possible diagnosis code combinations that match a service being provided. The system selects a product from a displayed set of products that match the service being provided, dynamically generates a set of medical necessities, and confirms the generated set of medical necessities. The system selects a product SKU based on the determined set of possible diagnosis code combinations, the selected product, and the confirmed set of medical necessities. The system dynamically generates confirmations based on DMEPOS standards, and confirms the generated confirmations by electronical signature of the physician, where the confirmation with signature is recorded with a time stamp. The physician electronically signs a recap of the prescription, and the patient confirms and electronically signs the generated set of confirmations.

1 Claim, 11 Drawing Sheets

< Erik Smith » New Prescription          Oakland ▾ | Erik Smith ≡

Diagnosis
Please choose a diagnosis below for a catheter order:

| Urinary Retention R33.9 | Urge Incontinence R32 |

Coude Diagnosis
If a coude catheter is required please choose an additional diagnosis below:

| Unspecified Urethral Stricture, Male N35.919 | Bladder Neck Obstruction N32.0 |
| Enlarged Prostate w/o Lower Urinary Tract Symptoms N40.0 | Enlarged Prostate w/Lower Urinary Tract Symptoms N40.1 |

Cancel    Next

FIG. 3

‹ Erik Smith » New Prescription                    Oakland ▾ | Erik Smith ≡

Choose a Product
Please choose a product for Erik's Urinary Retention diagnosis.

| Intermittent Straight Catheter A4351 | Intermittent Catheter Bag Attached A4353 |
| Intermittent Coude Catheter A4352 | Foley 2-way Coude Catheter A4340 |

Foley 2-way Straight Catheter A4338

Back    Next

FIG. 4

< Erik Smith » New Prescription          Oakland ▾   Erik Smith ≣

Choose a Product
Please choose a product for Erik's Urinary Retention diagnosis.

| Intermitten | | g Attached |
| Intermitten | Confirmed | atheter |

Medical Necessities Required
Intermittent Coude Catheter

All of the following are required:

- ⟨ Confirmed ⟩ Permanent (>3 mos) incontinence or retention ⊙
- ⟨ Confirmed ⟩ Ability to perform intermittent catheterization ⊙
- ⟨ Confirmed ⟩ Inability to pass a straight catheter ⊙

[ Cancel ]  [ Next ]

[ Back ]  [ Next ]

< Erik Smith » New Prescription       Oakland ▼ | Erik Smith ☰

Choose a Product Type
Please choose a type for Intermittent Coude Catheter

Hydrophilic
4 Products Available       ˅

| 14 FR | 16 FR | 18 FR |

Out of Formulary:
Hydrophilic

Non-Hydrophilic
4 Products Available       ›

Back    Next

FIG. 7

< Erik Smith » New Prescription                    Oakland ▾ | Erik Smith ☰

Prescription
Please confirm the prescription below and sign

| | | | |
|---|---|---|---|
| Group Practice: | Rx Redefined QA | Patient: | Erik Smith |
| Group DMEPOS: | 0000000000 | DOB | 06/01/1989 |
| Group NPI | 0000000000 | Gender | Male |
| Provider | Erik Smith | Address | 3860 MLK JR WAY |
| Provider NPI | 0000000000 | | OAKLAND CA 94609 |

Product & Diagnosis

Diagnosis
Urinary Retention (R33.9),     Length            Length
Bladder Neck Obstruction      Lifetime           08/13/2019
(N32.0)

Frequency                      Product
2 per Day = 60 per Month      Intermittent Coude Catheter Provider's Signature

[ Back ]  [ Next ]

FIG. 9

< Erik Smith  New Prescription   Oakland ▾ | Erik Smith

Provider Confirmation for Erik Smith

By signing below and pressing Next you confirm you understand the following:

> Confirmed

I acknowledge:

I am giving my written permission to Rx Redefined QA, its agents, affiliates, contractors, or service providers to contact me by telephone concerning the furnishing of the covered item that is to be purchased.

I agree that the provider has notified me and I understand that there are other options of companies that can provide medical supplies to me at home and I have a choice to utilize another supplier.

I agree that the provider has notified me of the product warranty information and I understand that I have received product warranty information.

I agree that the provider has notified me and I understand that if I have any questions or concerns with the product provided I should contact 510-383-6277

I agree that the provider has notified me and I understand that I have been provided with 30 unit(s) of A4352 on 2019-08-13 at 311 Oak Street Suite 2C, Oakland CA 94607 and, if applicable, my future orders of the product will be shipped to my address on file.

I agree that the provider has provided me the information on product instructions for use, product warranty information, contact information for Rx Redefined QA, the DMEPOS supplier standards, and information on or Rx Redefined QA's complaint resolution protocol.

Patient's Signature

[ Back ] [ Next ]

FIG. 10

SYSTEM AND PROCESS DISTRIBUTING PHYSICIAN-OWNED DURABLE MEDICAL EQUIPMENT (DME)

This application claims the benefit of priority of U.S. patent application Ser. No. 62/928,260, filed Oct. 30, 2019, which is hereby incorporated by reference in its entirety.

I. Field

Example aspects described herein generally relate to a providing a distribution platform for physician-owned Durable Medical Equipment (DMEs).

II. Background

Home medical equipment is a category of devices used for patients whose care is being managed from a home or other private facility managed by a nonprofessional caregiver or family member. It is often referred to as "durable" medical equipment (DME) as it is intended to withstand repeated use by non-professionals or the patient, and is appropriate for use in the home.

Traditionally, for most home medical equipment to be reimbursed by insurance, a patient must have a doctor's prescription for the equipment needed. Some equipment, such as oxygen, is FDA regulated and must be prescribed by a physician before purchase whether insurance reimbursed or otherwise.

Conventionally, the physician may recommend a supplier for the home medical equipment; otherwise, the patient will have to research this on their own.

Once a patient or caregiver selects an appropriate supplier, he/she presents the supplier with the prescription and patient's insurance information. The suppliers maintain an inventory of products and equipment, and fulfill the prescription, much like a Pharmacy.

BRIEF DESCRIPTION OF THE DRAWINGS

The features and advantages of the example embodiments of the invention presented herein will become more apparent from the detailed description set forth below when taken in conjunction with the following drawings.

FIGS. 3 to 10 illustrate different user interfaces implemented during the process of providing a distribution platform for physician-owned Durable Medical Equipment (DMEs).

DETAILED DESCRIPTION

The example embodiments presented herein are directed to providing a distribution platform for physician-owned Durable Medical Equipment (DMEs). This description is not intended to limit the application of the example embodiments presented herein. In fact, after reading the following description, it will be apparent to one skilled in the relevant art(s) how to implement the following example embodiments in alternative embodiments.

The disclosure herein provides for a logistics and distribution platform for physician-owned DMEs. These physicians sell durable medical equipment (catheters, orthotics, etc.) directly to their patients, rather than referring the order out to a third party DME supplier.

Figure 1:
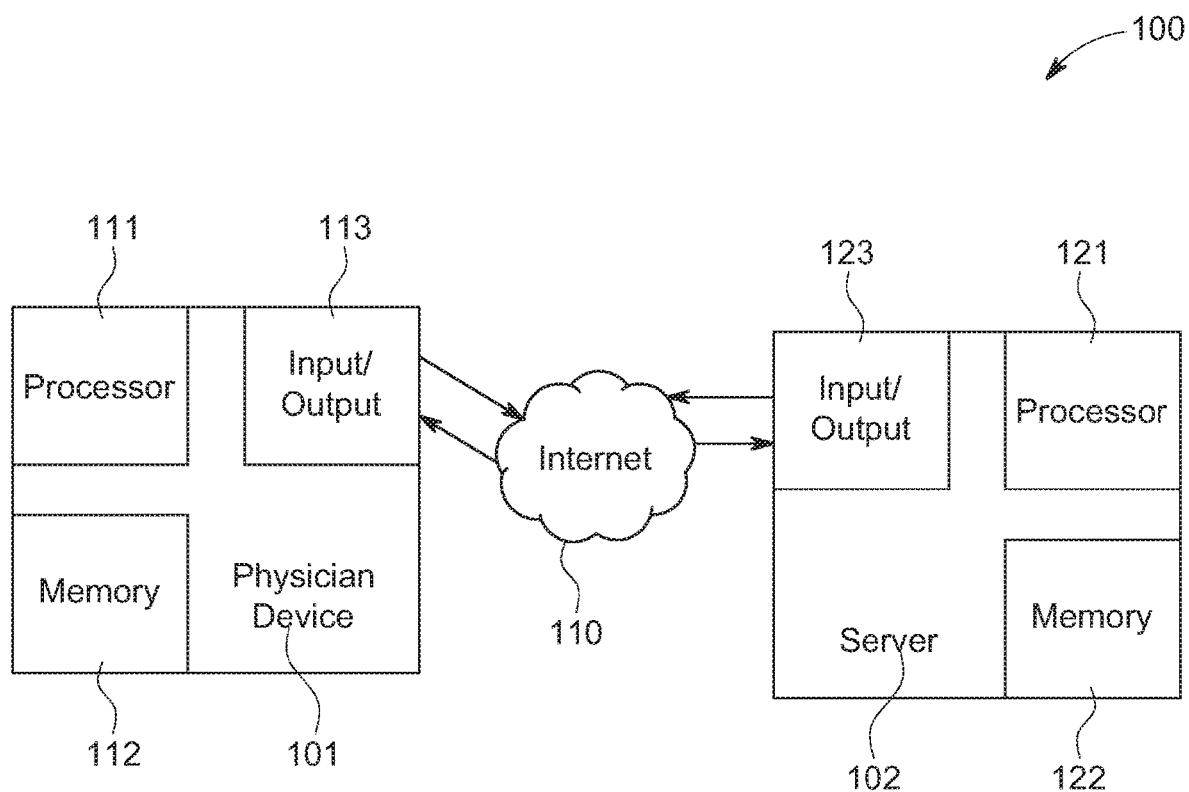
FIG. 1 illustrates an environmental view for providing a distribution platform for physician-owned Durable Medical Equipment (DMEs).

FIG. 1 illustrates an environmental view for providing the distribution platform for the physician-owned DMEs. As shown in FIG. 1, a system 100 includes a physician device 101, a server 102, and a network 110 such as the Internet. The physician device 101, the server 102 and the network 110 are used for implementing the techniques disclosed herein. The physician device 101 includes a processor 111, which can include one or more processing devices. Examples of processor 111 include without limitation a microprocessor, an application-specific integrated circuit (ASIC), a state machine, or other suitable processing device. Processor 111 is communicatively coupled to a computer-readable storage medium, such as memory 112, and accesses information stored in memory 112. Memory 112 also stores computer-executable instructions that when executed by processor 111 cause the processor 111 to perform the operations described herein. Memory 112 may be, for example, solid-state memories, optical and magnetic media or any other non-transitory machine-readable medium. Non-limiting examples of memory 112 include a hard drive, compact disc, flash memory, non-volatile memory, volatile memory, magnetic disk(s), etc. Physician device 101 also includes an input/output 113 including, for example, a wireless transmitter and a wireless receiver, and clock for generating timestamps.

The server 102 includes a processor 121, which can include one or more processing devices. Examples of processor 121 include without limitation a microprocessor, an application-specific integrated circuit (ASIC), a state machine, or other suitable processing device. Processor 121 is communicatively coupled to a computer-readable storage medium, such as memory 122, and accesses information stored in memory 122. Memory 122 also stores computer-executable instructions that when executed by processor 121 cause the processor 121 to perform the operations described herein. Memory 122 may be, for example, solid-state memories, optical and magnetic media or any other non-transitory machine-readable medium. Non-limiting examples of memory 122 include a hard drive, compact disc, flash memory, non-volatile memory, volatile memory, magnetic disk(s), etc. Server 102 also includes an input/output 123 including, for example, a wireless transmitter and a wireless receiver, and clock for generating timestamps.

FIG. 1 is merely one example of a particular implementation and is merely to illustrate the types of components that may be present in the platform. While the physician device 101 and the server 102 are illustrated with various components, it is not intended to represent any particular architecture or manner of interconnecting the components; as such details are not germane to the embodiments herein. It will also be appreciated that network computers, handheld computers, mobile phones, servers, and/or other data processing systems which have fewer components or perhaps more components may also be used with the embodiments herein. While the processes described, for example, in FIG. 2 described below can be implemented using the hardware of FIG. 1, the processes described herein are not limited to use with the hardware of FIG. 1.

The disclosure herein provides computer-based innovations which can allow physicians to write electronic prescriptions that are backed with documentation to 1) adhere to a set of legal Durable Medical Equipment, Prosthetics, Orthotics and Supplies (DMEPOS) standards, while 2) decreasing the rate of insurance denials during the billing process.

In the context of an electronic prescription and DME order, the embodiments described herein:

1) May keep physicians in compliance with DMEPOS standards. Throughout the electronic prescription and ordering process, the computer improvements of the platform can ensure the physician adheres to DMEPOS standards, documenting proof of each step. The platform captures electronic signature of both the physician and the patient being prescribed the products.

2) Decrease the rate of insurance denials by ensuring proper documentation of HCPC diagnosis codes and medical justifications required by insurance providers for the reimbursement of DME products. The computer advancements of the platform may ensure only DME products that fit the chosen diagnosis codes are prescribed—and if prescribed, the improved computer platform ensures proper medical justifications are documented by the physician.

Figure 2:
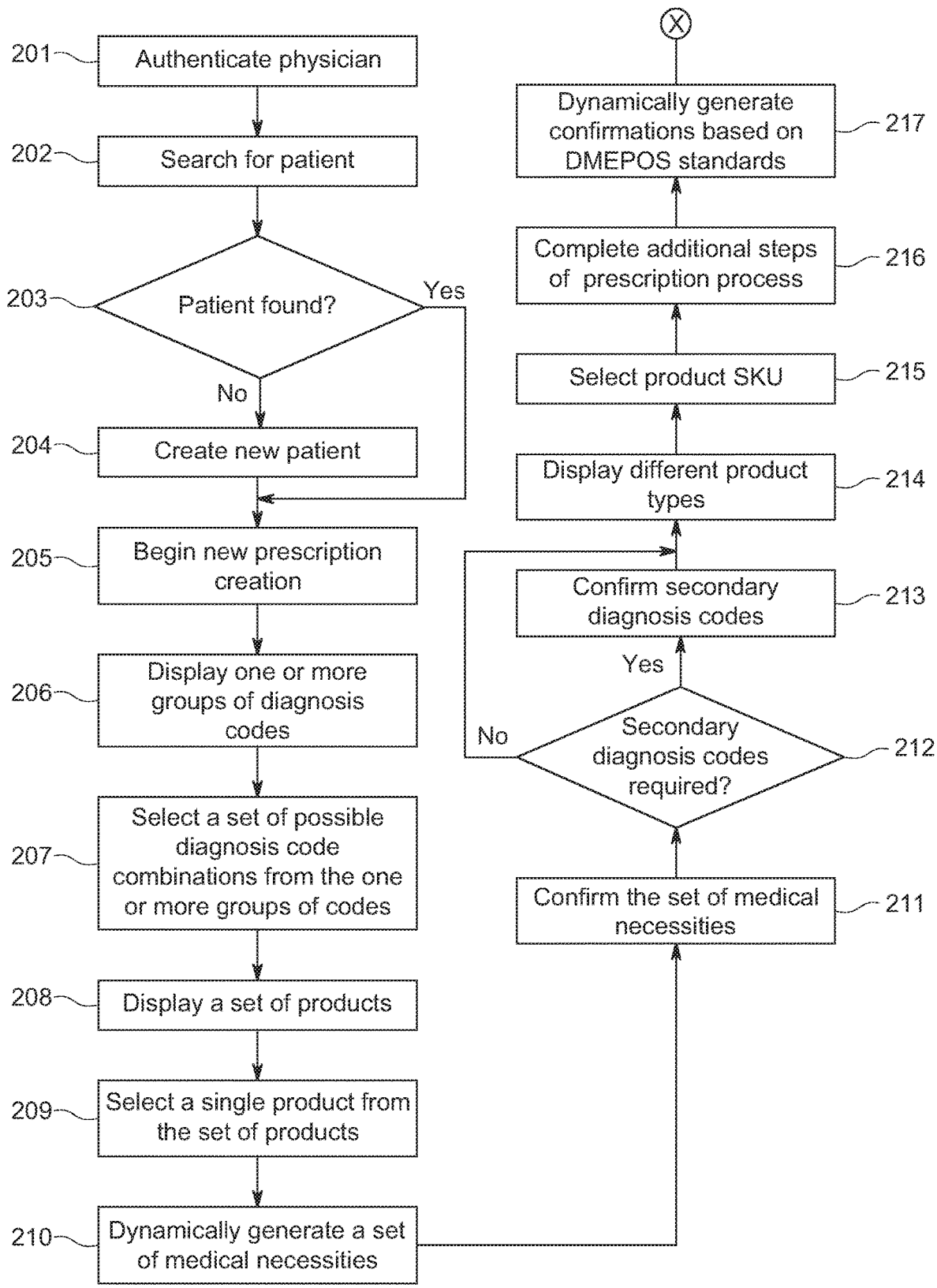
FIG. 2 is a flow chart for illustrating a process of providing a distribution platform for physician-owned Durable Medical Equipment (DMEs).
Figure 2:
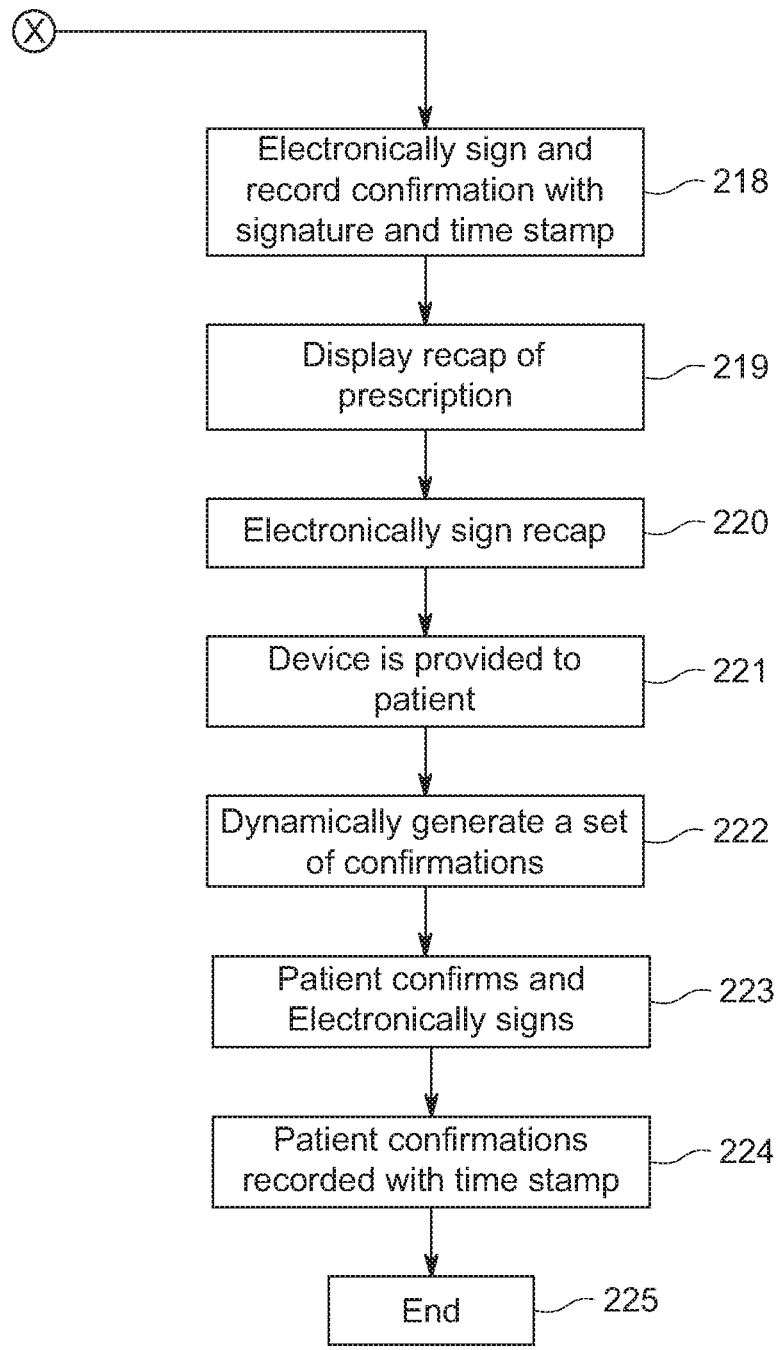

FIG. 2 shows a flow chart for illustrating a process of providing a distribution platform for physician-owned Durable Medical Equipment (DMEs), using the physician device 101 and server 102 shown in FIG. 1. Each process detailed in FIG. 2 can be performed by the physician device 101, the server 102, or a combination of both. As shown in FIG. 2, at 201, the physician authenticates themselves using the physician device 101. At 202, the physician searches, using the physician device 101, for a patient. If the patient is not found via the search at 203, then a new patient is created at 204. If the patient is found, then the process moves to block 205.

At 205, the physician begins the process of creating a new prescription for the selected patient, in the context of the patient's service needs (e.g., urology). At 206, one or more groups of diagnosis codes are displayed based on the new prescription, as shown, for example, in FIG. 3. At 207, the physician selects a set of possible diagnostic code combinations from the displayed one or more groups of codes, that match the service being provided. At 208, a set of products is displayed, as shown, for example, in FIG. 4. At 209, the physician selects a single product from the set of products that match the service need, to be prescribed to the patient.

At 210, a set of medical necessities are dynamically generated, as shown, for example, in FIG. 5. The set of medical necessities may be required as proof-of-need during the insurance reimbursement process. These necessities may be dynamically generated from one or more of the following criteria: (1) previously chosen diagnosis codes; (2) previously chosen product; and (3) date of last service for the current patient.

A set of diagnosis codes and products may be deemed "medically necessary" (also known as justifications) to be accepted by many insurance providers. The system herein assigns each product with logic parameters that must be validated, given various combinations of product and diagnosis codes. For example, in the set pseudocode below, the required medical necessities changes based on the total number of days since the last prescription was written for the patient. In this case, the system requires documentation that a non-routine change in product was required if the last prescription was written less than 30 days prior, alongside two other standard justifications that appear in all cases. {"justification": {"if": [{"<": [{"var": "days_since_last_prescription"}, 30]}, {"justify": [{"var": "justification"}, ["5c4da9a5", "00984416", "b1d51c0f"], [ ]]}, {"justify": [{"var": "justification"}, ["5c4da9a5", "00984416"], [ ]]}]}}

In other products, both diagnosis codes and justifications are required, as shown in the example pseudocode below. {"diagnosis": {"qualify": [{"var": "diagnosis"}, [ ], ["00061060", "4ea0d761", "ee4b9a9c", "7e14538a", "b5f8d3a4-566e"]]}, "justification": {"justify": [{"var": "justification"}, ["5c4da9a5", "9aef2f3e", "f95e27bf"], [ ]]}}

At 211, the physician then confirms or documents the set of medical necessities. Generally, once the justifications have been established, both the patients and providers sign dynamically generated "confirmations" which auto-populate with the validated diagnosis code, product, dates, etc. The confirmations are stored alongside digital signatures and timestamps of the patient and provider.

Figure 6:
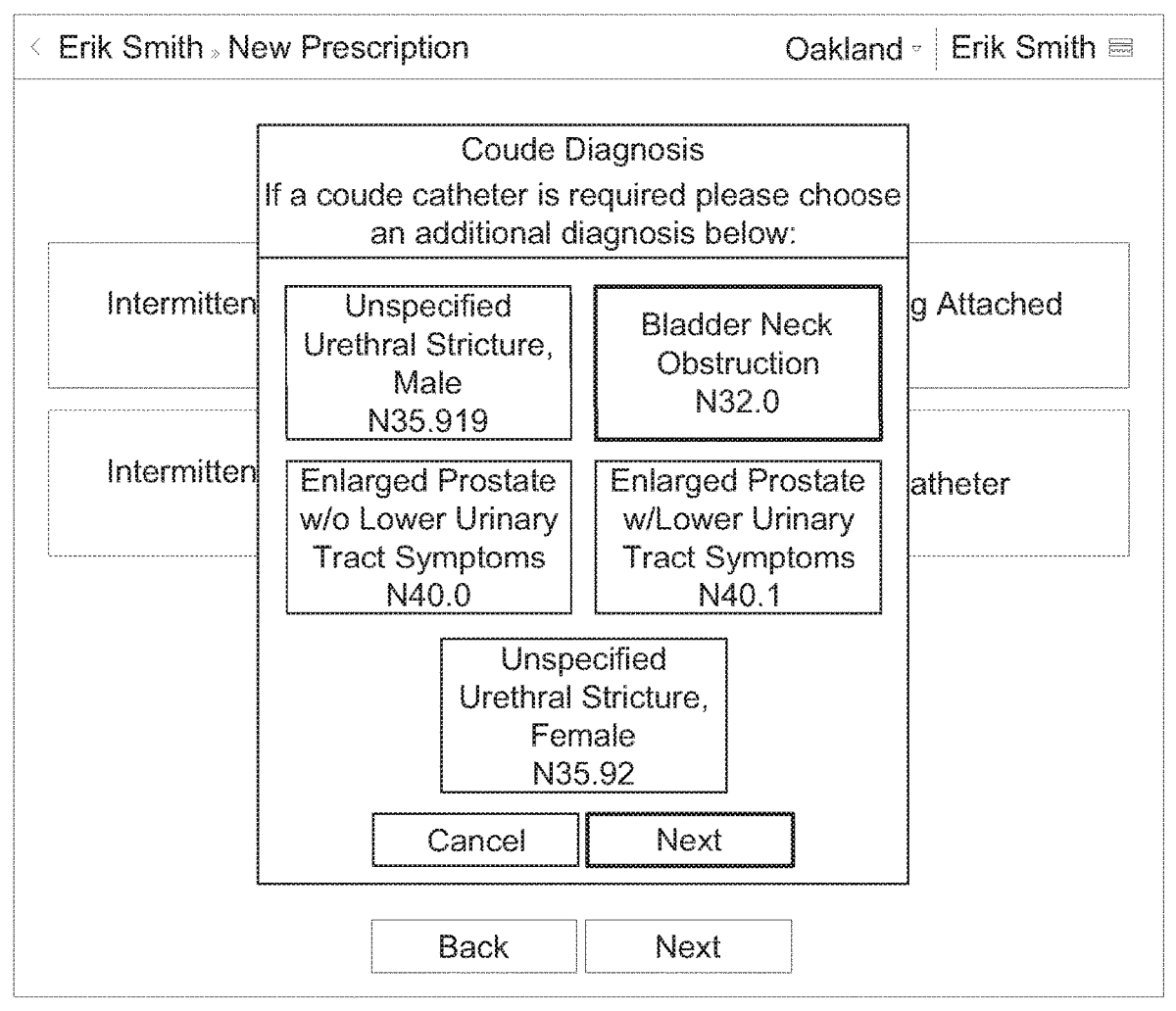

At 212, it is determined whether secondary diagnosis codes are required. If it is determined that secondary diagnosis codes are not required at 212, then the process moves to block 214. If it is determined that secondary diagnosis codes are required at 213, then the physician is prompted to confirm the secondary diagnosis codes, as shown, for example, in FIG. 6. Depending on previous selections, physician may be asked to further confirm and document secondary diagnosis codes required by the desired product.

Based on the foregoing blocks, at 214, different product types are displayed as shown, for example, at FIG. 7. Once the product, diagnosis, and medical necessities have been confirmed, the physician can choose a product SKU to be distributed to the patient (215). At 216, the physician may complete routine steps in the prescription process, including frequency of use, start date, and length of need.

Figure 8:

At 217, confirmations based on DMEPOS standards are dynamically generated as shown, for example, in FIG. 8. Again, once the justifications have been established, both the patients and providers sign dynamically generated "confirmations" which auto-populate with the validated diagnosis code, product, dates, etc. The confirmations are stored alongside digital signatures and timestamps of the patient and provider. The physician may be required to confirm the set of dynamically generated confirmations which may be required by the DMEPOS standards. The physician then electronically signs and the system records the confirmation with signature and time stamp (218).

At 219, a recap of the prescription is shown to the physician as shown, for example, in FIG. 9, and the physician electronically signs the recap (220). At 221, the physician device 101 is provided to the patient. At 222, a set of confirmations is dynamically generated as shown, for example, in FIG. 10. At 223, the patient confirms and signs the set of dynamically generated confirmations. At 224, the system records these confirmations with a time stamp. The process ends at 225. By nature of the computer improvements of the system, the process results physical products being provided to the patient directly through the physician, while complying with DMEPOS standards.

Some portions of the preceding detailed descriptions have been presented in terms of algorithms. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a mobile device, or similar electronic device, that manipulates and transforms data represented as physical (electronic) quantities within the system's registers and memories into other data similarly represented as physical quantities within the system memories or registers or other such information storage, transmission or display devices.

The processes and blocks described herein are not limited to the specific examples described and are not limited to the specific orders used as examples herein. Rather, any of the processing blocks may be re-ordered, combined or removed, performed in parallel or in serial, as necessary, to achieve the results set forth above. The processing blocks associated with implementing the system may be performed by one or more programmable processors executing one or more computer programs stored on a non-transitory computer readable storage medium to perform the functions of the system. All or part of the system may be implemented as, special purpose logic circuitry (e.g., an FPGA (field-programmable gate array) and/or an ASIC (application-specific integrated circuit)). All or part of the system may be implemented using electronic hardware circuitry that include electronic devices such as, for example, at least one of a processor, a memory, a programmable logic device or a logic gate. Further, processes can be implemented in any combination hardware devices and software components.

While certain embodiments have been described and shown in the accompanying drawings, it is to be understood that such embodiments are merely illustrative of and not restrictive, and are not limited to the specific constructions and arrangements shown and described, since various other modifications may occur to those of ordinary skill in the art. The description is thus to be regarded as illustrative instead of limiting.

What is claimed is:

1. A computer implemented method of providing a distribution platform for physician-owned Durable Medical Equipment (DMEs), the method comprising:
    authenticating a physician and selecting or creating a patient; determining a set of possible diagnosis code combinations that match a service being provided;
    selecting a product from a displayed set of products that match the service being provided;
dynamically generating a set of medical necessities;
confirming the dynamically generated set of medical necessities;
    selecting a product SKU based on the determined set of possible diagnosis code combinations, the selected product, and the confirmed set of medical necessities;
    dynamically generating confirmations based on DMEPOS standards, and confirming said dynamically generated confirmations by electronical signature of the physician, wherein the confirmation with signature is recorded with a time stamp;
electronically signing, by the physician, a recap of the prescription;
    dynamically generating a set of confirmations, and confirming and electronically signing, by the patient, the dynamically generated set of confirmations, wherein the confirmations are stored with a time stamp; and
    wherein in dynamically generating confirmations based on DMEPOS standards, once justifications have been established, both the patient and provider sign the dynamically generated confirmations which auto-populate with validated diagnosis code, product, and dates.

* * * * *